United States Patent [19]
Davis-Lemessy et al.

[11] Patent Number: 6,139,525
[45] Date of Patent: *Oct. 31, 2000

[54] FUSION BONDING OF CATHETER COMPONENTS

[75] Inventors: Patricia Andrea Davis-Lemessy, Santa Clara; Rebecca Ien Tavish, Santa Cruz, both of Calif.

[73] Assignee: Advanced Cardiovascular Systems, Inc., Santa Clara, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/889,489

[22] Filed: Jul. 8, 1997

[51] Int. Cl.$^7$ .................................................. A61M 29/00
[52] U.S. Cl. ............................ 604/103; 604/96; 604/915
[58] Field of Search ............................ 604/96, 280, 103, 604/912, 915, 523; 606/191, 194

[56] References Cited

U.S. PATENT DOCUMENTS

| | | | |
|---|---|---|---|
| 4,003,382 | 1/1977 | Dyke ..................................... | 128/349 B |
| 4,661,095 | 4/1987 | Taller et al. .............................. | 604/103 |
| 4,798,597 | 1/1989 | Vaillancourt ............................. | 604/270 |
| 4,886,689 | 12/1989 | Kotliar et al. ........................... | 428/35.7 |
| 4,950,239 | 8/1990 | Gahara et al. ............................ | 604/96 |
| 4,958,634 | 9/1990 | Jang ....................................... | 606/194 |
| 4,994,047 | 2/1991 | Walker et al. ............................ | 604/264 |
| 5,071,406 | 12/1991 | Jang ....................................... | 604/96 |
| 5,074,845 | 12/1991 | Miraki et al. ............................ | 604/101 |
| 5,195,969 | 3/1993 | Wang et al. .............................. | 604/96 |
| 5,256,145 | 10/1993 | Atkinson et al. ........................ | 604/96 |
| 5,267,959 | 12/1993 | Forman .................................... | 604/103 |
| 5,366,442 | 11/1994 | Wang et al. .............................. | 604/103 |
| 5,425,712 | 6/1995 | Goodin .................................... | 604/96 |
| 5,503,631 | 4/1996 | Onishi et al. ............................. | 604/96 |
| 5,538,510 | 7/1996 | Fontirroche et al. .................... | 604/265 |
| 5,549,552 | 8/1996 | Peters et al. ............................. | 604/96 |
| 5,554,120 | 9/1996 | Chen et al. ............................... | 604/96 |
| 5,587,125 | 12/1996 | Roychowdhury ...................... | 265/515 |
| 5,651,373 | 7/1997 | Mah ........................................ | 128/772 |
| 5,820,594 | 10/1998 | Fontirroche et al. .................... | 604/96 |
| 5,824,173 | 10/1998 | Fontirroche et al. .................... | 156/86 |
| 5,843,032 | 12/1998 | Kastenhofer ............................ | 604/96 |

FOREIGN PATENT DOCUMENTS

| | | |
|---|---|---|
| 94/23781 | 10/1994 | European Pat. Off. . |
| 697 219 | 2/1996 | European Pat. Off. . |
| 0 873 759 | 10/1998 | European Pat. Off. . |
| WO 92/19316 | 11/1992 | WIPO . |

OTHER PUBLICATIONS

A. H., Fitch, V.E. Bondybey, J.P. Vogt "Laser Bonding of Polymeric Materials" *The American Society of Mechanical Engineers*, 1–4 (Apr. 21–24, 1975).

Akira Miyamoto, Masami Sakurada, Kyoichi Mizuno, Akira Kurita, Haruo Nakamura "Application of Carbon Monoxide (CO) Laser for Laser Balloon Angioplasty" *SPIE—Optical Fibers in Medicine V* 1201:95–98 (1990).

Z. Syzmanski, J. Kurzyna "Spectroscopic Measurements of Laser Induced Plasma During Welding With $CO_2$ Laser" *Journal of Applied Physics*, 76(12):7750–7756 (Dec. 15, 1994).

F. O. Olsen "Pulsed Laser Materials Processing, ND–YAG versus $CO_2$ Lasers" *Annals of the CIRP* 44:141–145 (Jan. 1995).

*Primary Examiner*—Corrine McDermott
*Assistant Examiner*—Cris L. Rodriguez
*Attorney, Agent, or Firm*—Heller, Ehrman, White & McAuliffe

[57] ABSTRACT

The catheter of the invention generally has component parts made of polymeric materials and a fusion bond between these catheter parts containing a compatibilizing material which enhances the miscibility of the polymeric materials to facilitate the formation of the fusion bond. The catheter parts formed of polymeric materials may not be sufficiently miscible to readily form a fusion bond. The compatibilizing material increases the miscibility of the catheter parts in the molten state to effect the fusion bond between the polymeric materials. Chemical primer and plasma surface treatments may be used to provide the catheter parts to be bonded with functional groups which improve miscibility with the compatibilizing material.

10 Claims, 2 Drawing Sheets

FUSION BONDING OF CATHETER COMPONENTS

BACKGROUND OF THE INVENTION

This invention relates to the field of intravascular catheters, and more particularly to the means to sealingly affix catheter components together.

Intravascular balloon catheters such as those used in percutaneous transluminal angioplasty (PTA) and percutaneous transluminal coronary angioplasty (PCTA) generally have an inflatable balloon mounted along the distal region of the catheter, surrounding the catheter shaft. A catheter shaft lumen is configured for the delivery of inflation media to the interior of the balloon, to inflate the balloon once it is positioned at the desired location within the patient's vasculature.

Typically, the balloon catheter has an outer tubular member with a distal extremity terminating within the balloon interior and an inner tubular member with a distal extremity extending through and slightly beyond the distal end of the balloon. The annular space between the inner and outer members defines the inflation lumen in communication with the balloon interior. The integrity of the balloon interior is maintained, thereby enabling the balloon interior to hold inflation media, by fluid tight bonds located at proximal and distal extremities of the balloon which secure the balloon to the outer tubular member and the inner tubular member respectively. However, a variety of catheter designs are known. For example, the balloon can be coextruded with the catheter outer tubular member with a fluid tight bond securing the balloon distal extremity to the inner tubular member. Similarly, a single catheter shaft provided with a plurality of lumens can be used in place of the inner and outer membered shaft.

In the manufacture of balloon catheters, a number of techniques may be used to bond the balloon to the catheter shaft, including use of heat shrinkable balloon material, adhesives or fusion bonding. One attractive method of fusion bonding involves the use of laser energy. In this instance, the balloon and shaft mating surfaces are rapidly heated by a laser at the desired location of the bond. The temperature of the surfaces exposed to the intense and focused heat of the laser beam changes at a rate of approximately $10^{10}$ degrees C. per second. This heat from the application of the laser beam melts the interface of the two surfaces, which fuse together upon subsequently cooling down and a solid fusion bond is formed.

While laser bonding is a known technique for bonding balloons to catheter shafts, see for example U.S. Pat. No. 4,958,634 (Jang) and also U.S. Pat. No. 5,267,959 (Forman), one difficulty has been forming a balloon catheter using laser bonds between immiscible polymeric materials. Laser bonding typically requires the use of polymeric materials which are materially soluble or miscible when in the molten state. For example, materials from the same polymer family, such as polyethylene terephthalate (PET) and HYTREL® which are both polyesters, will form strong laser bonds together, whereas, PET and nylon will not.

Laser bonding provides bonds suitable for use in balloon catheter manufacture which are fluid tight, and sufficiently strong to withstand the fluid pressures produced by the inflation media which sometimes can exceed 400 psi. Moreover, because laser bonding generally provides superior repeatability in manufacturing, it is a preferred bonding method. However, because the ideal catheter shaft and balloon materials are chosen based on factors such as strength, flexibility and stiffness, the ideal materials are not necessarily compatible polymeric materials capable of being effectively fusion bonded together. Therefore, what has been needed is the ability to fusion bond dissimilar materials together to form the invention claimed, which is a catheter with a fusion bond. The present invention satisfies these and other needs.

SUMMARY OF THE INVENTION

The invention is directed to a catheter having a first polymeric component fusion bonded to a second polymeric component.

The catheter of the invention generally has a first catheter part formed of a first polymeric material and a second catheter part formed of a second polymeric material fusion bonded to the first catheter part, with the fusion bond containing a compatibilizing material which enhances the miscibility of the polymeric materials during the fusion bonding. Although the polymer materials of the catheter parts may not be compatible and therefore completely miscible in the molten state, a fusion bond is formed due to the compatibilizing material which is itself miscible with the polymeric materials of both catheter parts in the molten state.

In one aspect of the invention, the catheter of the invention is a balloon catheter generally having an elongated catheter shaft comprising at least one tubular member with at least one lumen extending therein. An inflatable balloon on a distal portion of the shaft has an interior in fluid communication with the shaft lumen. The balloon is secured to the catheter shaft by one or more fusion bonds, as when a distal skirt of the balloon is sealed about and secured to a tubular member of the catheter shaft by a distal fusion bond, and a proximal skirt of the balloon is sealed about and secured to the catheter shaft by a proximal fusion bond at a point proximal to the distal fusion bond. Alternatively, the balloon may be formed from the same tubing as the catheter shaft with the distal skirt of the balloon sealed about and secured to the distal end of an inner tubular member of the catheter by a single fusion bond.

A compatibilizing agent is provided between the shaft and balloon which facilitates the laser bonding of the balloon to the shaft. Even if the shaft and balloon are made of dissimilar polymeric materials which normally are not capable of being fusion bonded together, a fluid tight fusion bond can be created by selecting the compatibilizing agent that generates sufficient miscibility between the two dissimilar polymer materials so that an effective fusion bond can be formed between the two. The shaft and balloon are bonded together when heat is applied which is sufficient to melt the opposed surfaces with the compatibilizing agent present between the two members. The melted materials are subsequently allowed to cool down and solidify into a fusion bond containing the compatibilizing material.

The compatibilizing agent must be in intimate contact with both the balloon and shaft surfaces for the fusion bond to form. In one presently preferred embodiment, well known extrusion techniques are used to form a polymer compatibilizer as a short cylindrical collar configured to be slidingly received within the annular interface between the catheter shaft and balloon. Alternatively, the compatibilizing agent can be in a solution which is solvent cast onto the surface of the catheter shaft and/or balloon using conventional techniques for applying solutions to surfaces, such as spraying, dipping or painting, or the compatibilizing agent may be added as an integral co-component of one or both of the catheter parts.

The compatibilizing agent, which is the compatibilizing material prior to fusion bonding, melts along with the balloon and shaft surfaces during fusion bonding. After cooling, the fusion bond is formed which contains balloon, shaft, and compatibilizing material intimately intermixed with no remaining compatibilizing agent independent of the shaft and balloon material. The compatibizing agent interface with the balloon and shaft surfaces is fused to each of the balloon and shaft. A balloon-compatibilizer-shaft interface is thereby created by the fusion bond which results in a fused molten polymer interface.

The polymer compatibilizing agent may be used alone or in combination with a surface treatment of one or both of the opposed surfaces to provide improved miscibility with the compatibilizing agent. In accordance with one embodiment of the invention, the surface treatment consists of a plasma treatment applied to either the surface of the balloon, the surface of the shaft, or both. A suitable plasma treatment is achieved from a 100% Argon plasma stream at about 200 watts power applied to the surfaces for about 8 minutes. Alternatively, the surface treatment may consist of a chemical primer applied to the surfaces of the balloon and shaft. Suitable chemical primers are LOCTITE PRISM 7701, containing butoxy-propanol, and LOCTITE PRISM 794, containing n-heptane. The surface treatment acts by providing functional groups, and in some cases increased surface area on the shaft and balloon surfaces, which facilitates fusion bond formation between the compatibilizing agent and the shaft and balloon.

In accordance with one aspect of the invention, the shaft and balloon are made from materials which may not be readily miscible in the molten state. For example, the shaft may be made from a material in the polyethylene family of polymers such as high density polyethylene (HDPE), while the balloon is a polyamide material such as nylon. A presently preferred shaft material selected from the group consisting of polyesters, polyolefins, and polyamides, such as is a flexible material such as HDPE, or HYTREL® which is available from DUPONT. A presently preferred balloon material selected from the group consisting of polyesters, and polyamides such as is nylon. These preferred materials from different polymer families could not be readily fusion bonded together without the compatibilizing material. In accordance with the invention, the compatibilizing agent or material is a polymer which is capable of forming fusion bonds to both the shaft and balloon. One group of presently preferred polymer compatibilizing agents are hot melt adhesives which are miscible in the molten state with the preferred catheter materials discussed above. These presently preferred polymer compatibilizing agents or material by trade name and chemical structure, include ADMER NF 482A, a functionalized polyolefin; LOTADAR 3700, an ethylene acrylic ester maleic anhydride; MORTHANE CA 100-200 and CA-116, a hot melt polyurethane; and PRIMACOR 1420, an ethylene and acrylic acid copolymer.

The method of forming a fusion bond between the shaft and balloon involves positioning the catheter shaft and balloon in surrounding relation to one another, and positioning the compatibilizing agent between the balloon and shaft so that it contacts both the balloon and shaft surfaces. For example, a compatibilizing agent in the shape of a collar, i.e. a hollow tube, may be slidingly mounted on the catheter shaft between the shaft and balloon at the desired location of the fusion bond, and a skirt of the balloon disposed around the compatibilizing agent and catheter shaft. Heat sufficient to melt the polymeric materials is then controllably directed at the location of the bond, and the materials are allowed to cool and solidify to form a fusion bond. The presently preferred fusion heat source for producing the fusion bonds is a $CO_2$ laser. The preferred laser power is about 140 mW.

In a presently preferred embodiment, a sheath is provided around the balloon skirt, compatibilizing agent, shaft assembly, before the area is exposed to the fusion heat source. This sheath provides an external force on the catheter components, thus ensuring intimate contact between the materials as they melt together. A suitable sheath is tubing formed of a heat shrinkable material such as a fluoropolymer.

In the presently preferred embodiment, the catheter of the invention has a catheter shaft and balloon made from dissimilar materials, yet bonded together by a fluid tight fusion bond. This produces a catheter with superior trackability and smaller, softer catheter tips, due to the short and flexible fusion bond. Catheter designs which use two dissimilar materials such as nylon and HDPE, but which do not incorporate fusion bonds, must resort to bonding techniques such as adhesive bonds between these materials. This compromises catheter tractability due to the longer bond lengths needed for adhesive bonds, and produces a stiff catheter distal extremity which would preferably be made softer for maneuverability and vascular trauma prevention. Moreover, because laser bonding generally provides superior repeatability in manufacturing, it is a preferred bonding method. Balloon catheters made using coextruded members have similar drawbacks to adhesive bonding. For example, even though a catheter shaft made from HDPE coextruded with a nylon coating could be fusion bonded to a nylon balloon, the coextruded shaft tends to be disadvantageously stiff. Finally, the fusion bonded balloon catheter of the invention has low profiled catheter tips for improved maneuverability. These and other advantages of the invention will become more apparent from the following detailed description of the invention and the accompanying exemplary drawings.

DETAILED DESCRIPTION OF THE INVENTION

Figure 1:
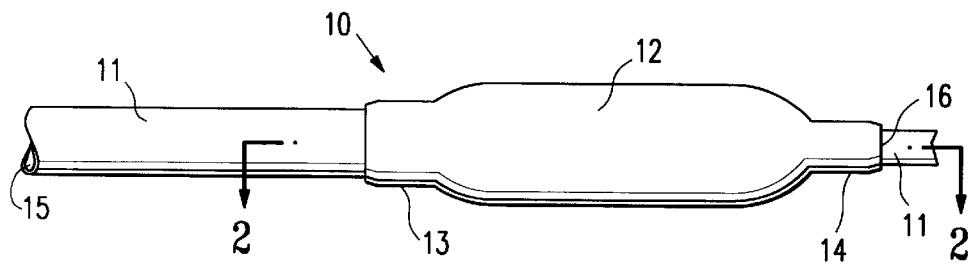
FIG. 1 is an elevational view of a balloon catheter which embodies features of the invention.

In the embodiment illustrated in FIG. 1, the catheter 10 of the invention is a balloon catheter having an elongated catheter shaft 11 with an inflatable balloon 12 on a distal portion of the shaft. The balloon 12 is sealingly secured to the shaft 11 by one or more fusion bonds. For example, the catheter is provided with either a proximal fusion bond 13 located at the balloon proximal extremity, a distal fusion bond 14 at the balloon distal extremity, or both. The shaft lumen 15 is in fluid communication with the balloon interior 16.

Figure 2:
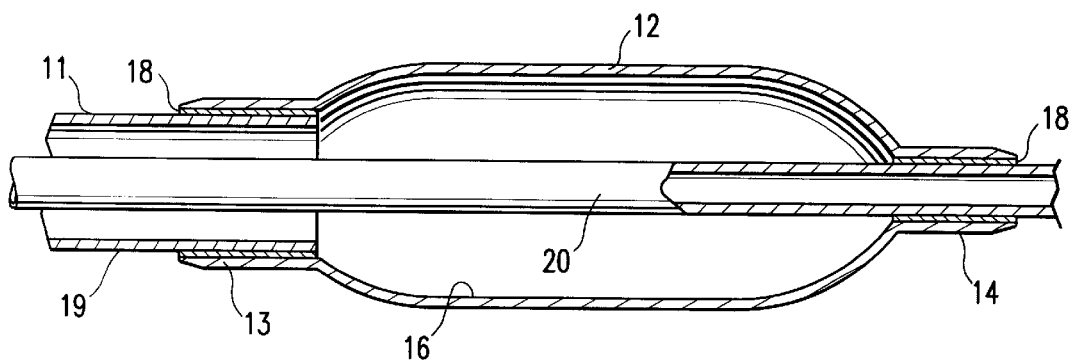
FIG. 2 is a longitudinal cross-sectional view of the catheter shown in FIG. 1 within the lines 2—2.

The fusion bond is formed at an interface between the shaft and balloon. As shown in FIG. 2, a compatibilizing agent 18, which enhances the miscibility of the polymeric materials during fusion bonding of the balloon to the shaft, is located between the shaft and balloon at the desired location of the fusion bonds 13 and 14 prior to fusion bonding. The compatibilizing agent 18 is in surrounding relation to both the balloon 12 and shaft 11 surfaces. The fusion bond 13, 14 formed by the application of fusion heat contains the compatibilizing material.

In the embodiment illustrated in FIG. 2, the catheter shaft 11 comprises an outer tubular member 19 and an inner tubular member 20. The balloon 12 is fusion bonded to the outer tubular member 19 by the proximal fusion bond 13, and to the inner tubular member 20 by the distal fusion bond 14. In an alternative embodiment illustrated in FIG. 3, a coextruded balloon and catheter shaft 21 is fusion bonded to the shaft inner tubular member 20 by the distal fusion bond 14.

To form the fusion bond, the compatibilizing agent 18 must intimately contact both the balloon 12 and shaft 11 surfaces. In the embodiment illustrated in FIG. 4, shrink tubing 22 surrounds the interface between the shaft 11, compatibilizer 18 and balloon 12 surfaces, and forces the surfaces into intimate contact prior to exposure to the laser energy. The strength of the fusion bond that the compatibilizing agent forms with the balloon and shaft can be improved by providing a primer or a functionalizing treatment on the surface of the balloon and shaft (not shown).

Figure 3:
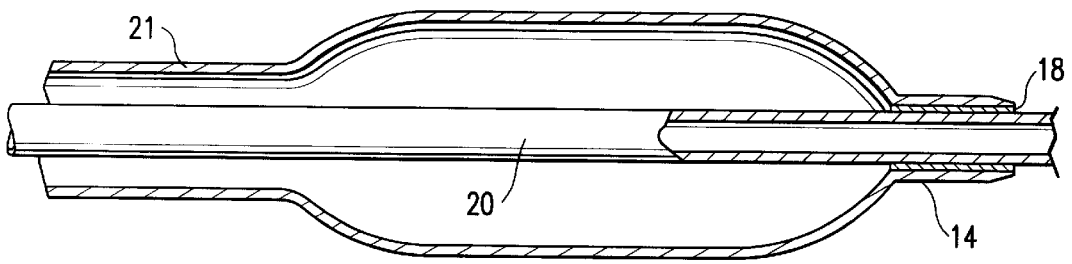
FIG. 3 is a longitudinal cross-sectional view of an alternative embodiment of a balloon catheter which embodies features of the invention.
Figure 4:
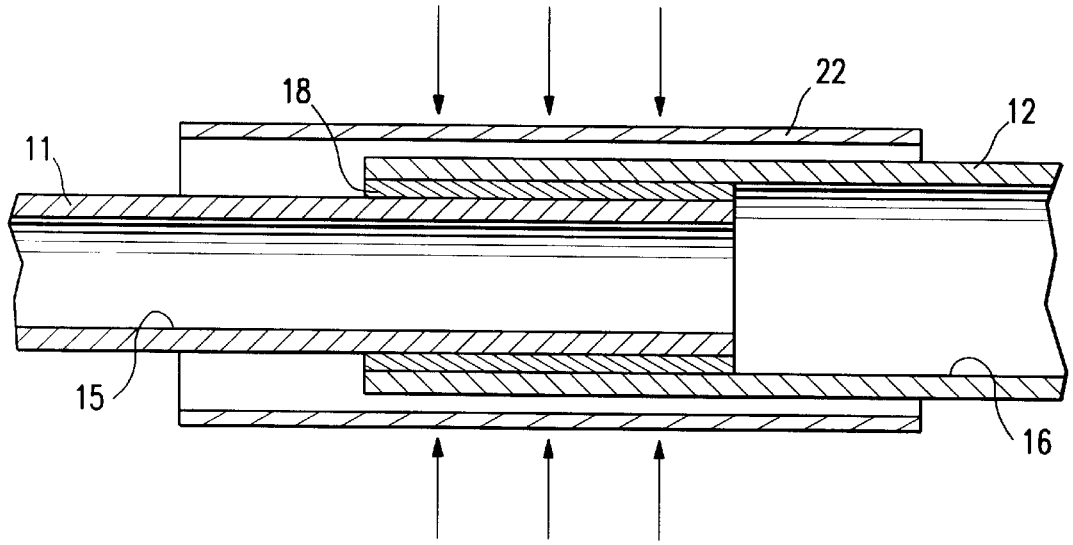
FIG. 4 is an enlarged longitudinal cross-sectional view of one embodiment of the invention showing a fused interface between the balloon and catheter shaft.
Figure 5:
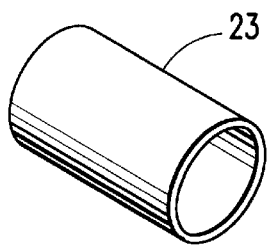
FIG. 5 is an elevational view of one embodiment of the compatibilizer of the invention.

In the embodiment illustrated in FIGS. 2, 3, and 4, the compatibilizing agent 18 contacts the outer wall of the shaft and inner wall of the balloon. The compatibilizing agent 18 may have been applied as a solution to the member surfaces to be bonded, or as a cylindrical collar formed at least in part of compatibilizing agent which was disposed around the catheter shaft. As illustrated in more detail in FIG. 5, when the compatibilizing agent is formed as a cylindrical collar 23, it is configured to be slidingly received in the annular interface between the catheter shaft and balloon. When the compatibilizer is applied by dipping the substrate surfaces into a solution of the compatibilizing agent 18, the compatibilizing agent may be applied to both the inner and outer surfaces of the substrates (not shown). Whether applied as a solution or as a solid, the compatibilizing agent thickness should range from about 0.5 mm to about 4.0 mm, and the compatibilizing agent length is sized to approximate the desired fusion bond length which should be about 5.0 mm to about 25 mm.

Figure 6:
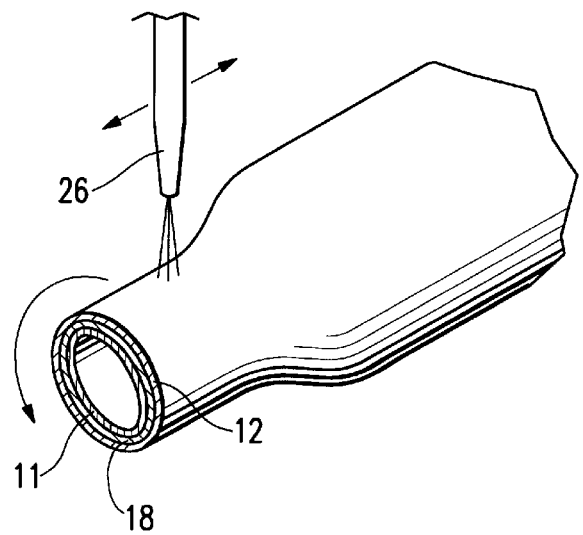
FIG. 6 illustrates fusion heat application during fusion bond formation in a catheter which embodies features of the invention.

In the method of forming the balloon catheter 10 of the invention, the compatibilizing agent 18 is provided in contact with the surfaces of the balloon 12 and catheter shaft 11 at the desired location of the fusion bond. The shrink tubing 22 is then placed around the balloon, compatibilizer, shaft assembly interface and heated to induce shrinking and form a tight fit between the surfaces to be bonded. Heat sufficient to melt the substrates is controllingly directed from a heat source 26 to the assembly interface, as illustrated in FIG. 6. As mentioned above, the presently preferred fusion heat source is a $CO_2$ laser. The laser power is about 50 mW to about 250 mW, the laser rotation speed about the members to be bonded is about 75 to about 300, and the laser absolute focus is about 0.30 to about 0.50. The materials are heated at temperatures between about 100° C. to about 200° C. for about 30 to about 150 seconds. The melted substrates are then allowed to cool down and fuse together into a fusion bond.

EXAMPLE

A nylon balloon and HDPE shaft were bonded together at a proximal juncture using PRIMACOR 1420 as the compatibilizing agent. The heat source was a $CO_2$ laser set at 140 mW power, 0.35 absolute focus, and a rotation speed of 250. 10 samples resulted, having a fused bond containing a compatibilizing material, with an average rupture failure pressure of 496 psi with a standard deviation of 25 psi. None of the failures were at the proximal seal formed by the fused bond.

While the invention has been described in terms of certain embodiments, modifications and improvements may be made to the invention. For example, while the fusion bonds described were between a balloon and catheter shaft, a variety of catheter components made of polymers may be fusion bonded together in accordance with the invention. Also, the compatibilizing agent 18 may be used to enhance the miscibility of polymers of various degrees of miscibility with one another, ranging from miscible to completely immiscible together. Additionally, any number of balloon catheter designs may be used, and the orientation of the balloon and shaft may be varied as when the shaft is slidingly disposed over the balloon. Other modifications may be made without departing from the scope thereof.

What is claimed is:

1. A catheter assembly, comprising:
    a) a first catheter part formed of a first polymeric material;
    b) a second catheter part having a bonded section fusion bonded to the first catheter part, and a nonbonded section, the bonded and nonbonded sections being formed of a blend of a second polymeric material and a compatibilizing material, the compatibilizing material being a hot melt adhesive fusion bondable to the first and second polymeric materials.

2. The catheter assembly of claim 1 wherein
    a) the first catheter part comprises an elongated shaft; and
    b) the second catheter part comprises an inflatable balloon secured to the catheter shaft.

3. The catheter of claim 2 wherein the balloon is a dilatation balloon.

4. The catheter of claim 1 wherein the first polymeric material is chosen from the group consisting of polyesters, polyolefins, and polyamides.

5. The catheter of claim 1 wherein the second polymeric material is chosen from the group consisting of polyamides and polyesters.

6. The catheter of claim 1 wherein the first polymeric material is selected from the group consisting of polyethylene and polyester, and the second polymeric material comprises nylon.

7. The catheter of claim 1 wherein the first polymeric material is incompatible with the second polymeric material.

8. The catheter of claim 1 wherein the compatibilizing material prior to formation of a fusion bond is a compatibilizing agent that is a hot melt adhesive polymer comprising a fusion bonding functional group selected from the group consisting of functionalized polyolefin, ethylene acrylic ester maleic anhydride, hot melt polyurethane, and ethylene acrylic acid copolymer groups, wherein the functional group is capable of forming a fusion bond with a polymer selected from the group consisting of polyester, polyolefin, and polyamide.

9. A balloon catheter, comprising:
    a) a polymeric elongated shaft having proximal and distal ends and at least one lumen extending therein and formed of a polymeric material;
    b) a polymeric inflatable balloon formed of a polymeric material and secured to the catheter shaft, having proximal and distal ends and an interior in fluid communication with the lumen of the catheter shaft, at least one of the shaft and balloon being formed of a blend of a polymeric material and a compatibilizing material, the compatibilizing material being formed of a hot melt adhesive fusion bondable to the shaft polymeric material and the balloon polymeric material; and c) at least one fused bond between the catheter shaft and the balloon, containing the compatibilizing material.

10. The catheter of claim 9 wherein the compatibilizing material prior to formation of a fusion bond is a compatibilizing agent that is a hot melt adhesive polymer comprising a fusion bonding functional group selected from the group consisting of functionalized polyolefin, ethylene acrylic ester maleic anhydride, hot melt polyurethane, and ethylene acrylic acid copolymer groups, wherein the functional group is capable of forming a fusion bond with a polymer selected from the group consisting of polyester, polyolefin, and polyamide.

* * * * *

UNITED STATES PATENT AND TRADEMARK OFFICE
CERTIFICATE OF CORRECTION

PATENT NO. : 6,139,525
DATED : October 31, 2000
INVENTOR(S) : Patricia Andrea Davis-Lemessy, Rebecca Ien Tavish It is certified that error appears in the above-identified patent and that said Letters Patent is hereby corrected as shown below:

<u>Title page,</u>
Under "References Cited FOREIGN PATENT DOCUMENTS":

After "WO  92/19316     11/1992     WIPO", insert
-- WO  95/09667      4/1995     WIPO --.

Signed and Sealed this

Twenty fifth Day of September, 2001

Attest:

*Attesting Officer*

NICHOLAS P. GODICI
*Acting Director of the United States Patent and Trademark Office*